(12) United States Patent
Kim et al.

(10) Patent No.: US 10,750,279 B2
(45) Date of Patent: Aug. 18, 2020

(54) SIGNAL PROCESSING DEVICE AND SIGNAL PROCESSING METHOD FOR DETECTION OF DIRECTION OF MOVEMENT OF A REGION

(71) Applicant: SONY CORPORATION, Tokyo (JP)

(72) Inventors: Heesoon Kim, Kanagawa (JP);
Tatsushi Nashida, Kanagawa (JP);
Takumi Suzuki, Kanagawa (JP);
Masaharu Yoshino, Saitama (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/330,281

(22) PCT Filed: Sep. 25, 2017

(86) PCT No.: PCT/JP2017/034552
§ 371 (c)(1),
(2) Date: Mar. 4, 2019

(87) PCT Pub. No.: WO2018/070232
PCT Pub. Date: Apr. 19, 2018

(65) Prior Publication Data
US 2019/0208321 A1    Jul. 4, 2019

(30) Foreign Application Priority Data

Oct. 14, 2016  (JP) ................................ 2016-202737
Feb. 23, 2017  (JP) ................................ 2017-031873

(51) Int. Cl.
*H04R 3/00* (2006.01)
*H04R 1/40* (2006.01)
*A61B 5/11* (2006.01)
*G01P 13/04* (2006.01)
*A61B 5/00* (2006.01)

(52) U.S. Cl.
CPC ............ *H04R 3/005* (2013.01); *A61B 5/1122* (2013.01); *A61B 5/6824* (2013.01);
(Continued)

(58) Field of Classification Search
CPC .......... G01P 13/045; G01P 5/24; G01P 5/241; G01P 5/245; H04R 3/005; H04R 1/406;
(Continued)

(56) References Cited

U.S. PATENT DOCUMENTS 9,121,860 B1    9/2015 Cronyn
2005/0131591 A1*  6/2005 Drutowski .............. G01P 5/245
                                                       701/3

(Continued)

FOREIGN PATENT DOCUMENTS

CN    103877715 A    6/2014
JP    51-121680 A    10/1976
(Continued)

OTHER PUBLICATIONS

International Search Report and Written Opinion of PCT Application No. PCT/JP2017/034552, dated Dec. 19, 2017, 08 pages of ISRWO.

*Primary Examiner* — Jason R Kurr
(74) *Attorney, Agent, or Firm* — Chip Law Group

(57) ABSTRACT

Provided is a signal processing device including a plurality of sound collection units that is arranged at given positions, and a detection unit configured to detect, from respective sounds that have occurred in accordance with a movement of a region to which attachment is performed and have been collected by the sound collection units, a direction of the movement of the region.

14 Claims, 17 Drawing Sheets

(52) U.S. Cl.
CPC ............ *G01P 13/045* (2013.01); *H04R 1/406* (2013.01); *A61B 5/6829* (2013.01); *A61B 2562/0204* (2013.01); *H04R 2201/401* (2013.01); *H04R 2499/11* (2013.01); *H04S 2400/11* (2013.01); *H04S 2400/15* (2013.01)

(58) Field of Classification Search
CPC .......... H04R 2201/401; H04R 2499/11; H04R 23/00; H04R 2201/023; H04S 2400/11; H04S 2400/15; A61B 5/1122; A61B 5/6824; A61B 5/6829; A61B 2562/0204; G01L 13/025; G01L 15/00
See application file for complete search history.

(56) References Cited

U.S. PATENT DOCUMENTS

| | | | |
|---|---|---|---|
| 2012/0173191 A1* | 7/2012 | Moeller | G01P 5/22 702/142 |
| 2014/0180632 A1 | 6/2014 | Yataka | |
| 2016/0003698 A1* | 1/2016 | Wiesbauer | G01L 13/025 381/174 |

FOREIGN PATENT DOCUMENTS

| | | |
|---|---|---|
| JP | 2010-281279 A | 12/2010 |
| JP | 2014-121456 A | 7/2014 |
| KR | 10-2014-0081695 A | 7/2014 |

\* cited by examiner

SIGNAL PROCESSING DEVICE AND SIGNAL PROCESSING METHOD FOR DETECTION OF DIRECTION OF MOVEMENT OF A REGION

CROSS REFERENCE TO RELATED APPLICATIONS

This application is a U.S. National Phase of International Patent Application No. PCT/JP2017/034552 filed on Sep. 25, 2017, which claims priority benefit of Japanese Patent Application No. JP 2016-202737 filed in the Japan Patent Office on Oct. 14, 2016 and also claims priority benefit of Japanese Patent Application No. JP 2017-031873 filed in the Japan Patent Office on Feb. 23, 2017. Each of the above-referenced applications is hereby incorporated herein by reference in its entirety.

TECHNICAL FIELD

The present disclosure relates to a signal processing device and a signal processing method.

BACKGROUND ART

There exists a technology of detecting a movement of an attachment region of a motion sensor on the basis of sensing data output by the motion sensor including an accelerator sensor, an angular velocity sensor, and the like (see Patent Literature 1, for example).

CITATION LIST

Patent Literature

Patent Literature 1: JP 2015-159383A

DISCLOSURE OF INVENTION

Technical Problem

When an object is moved, an air flow occurs. If such an air flow is regarded as sound, it is considered that the movement of an object can be detected without using a motion sensor.

Then, the present disclosure proposes a new and improved signal processing device and signal processing method capable of detecting the details of a movement from sounds that occur in accordance with the movement.

Solution to Problem

According to the present disclosure, there is provided a signal processing device, including: a plurality of sound collection units that is arranged at given positions; and a detection unit configured to detect, from respective sounds that have occurred in accordance with a movement of a region to which attachment is performed and have been collected by the sound collection units, a direction of the movement of the region.

Moreover, according to the present disclosure, there is provided a signal processing method, including: detecting, on the basis of respective sounds that have been collected by a plurality of sound collection units arranged at given positions and have occurred in accordance with a movement of a region to which the sound collection units are attached, a direction of the movement of the region.

Advantageous Effects of Invention

According to the present disclosure described above, it is possible to provide a new and improved signal processing device and signal processing method capable of detecting the details of a movement from sounds that occur in accordance with the movement.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
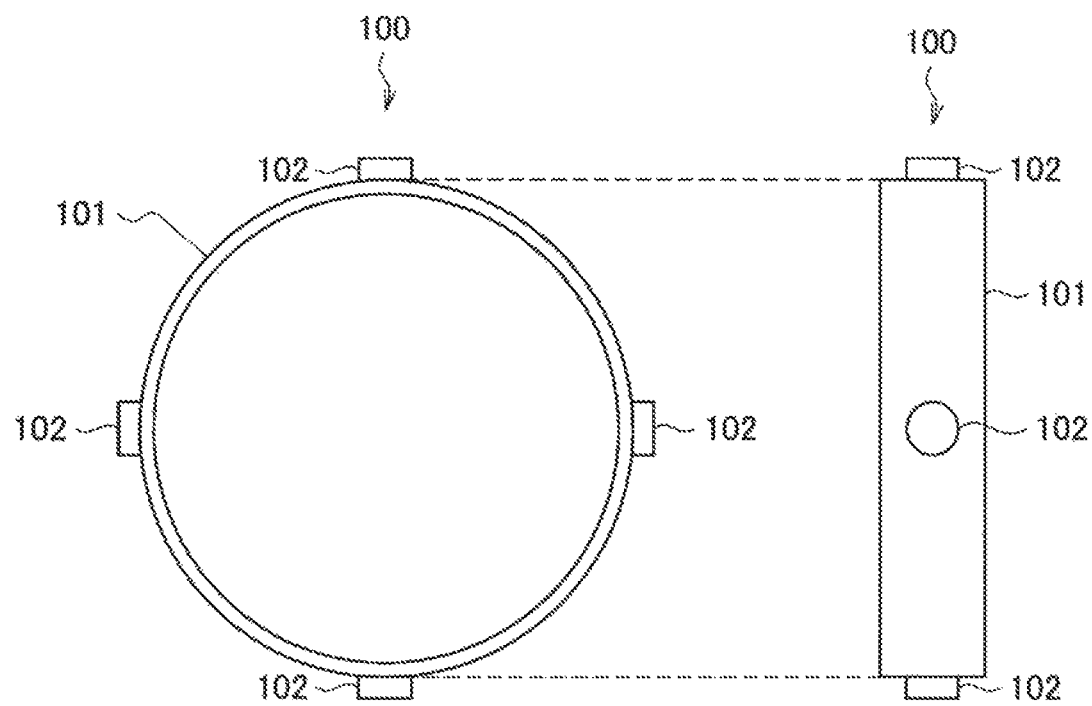
FIG. 1 is an explanatory diagram illustrating an example of an external appearance of a signal processing device 100 according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be given in the following order.
1. Embodiment of present disclosure
1.1. Example of external appearance
1.2. Example of functional configuration
1.3. Application example
2. Summary

1. Embodiment of Present Disclosure

1.1. Example of External Appearance

An embodiment of the present disclosure will be described in detail. First, an example of an external appearance of a signal processing device according to an embodiment of the present disclosure will be described.

FIG. 1 is an explanatory diagram illustrating an example of an external appearance of a signal processing device 100 according to an embodiment of the present disclosure. The following will describe an example of an external appearance of the signal processing device 100 according to the embodiment of the present disclosure using FIG. 1.

The signal processing device 100 according to the embodiment of the present disclosure illustrated in FIG. 1 is a device that can be attached at a region or an object to be moved such as a wrist, an ankle, or the like of a human, for example. An object at which the signal processing device 100 is attached can be sporting goods, for example, such as a bat, a racket, and a golf club, for example. Then, the signal processing device 100 is a device provided with a plurality of microphones to detect a moving direction to which the signal processing device 100 is attached on the basis of a level of aerodynamic sound (wind noises) collected by the microphones.

As illustrated in FIG. 1, the signal processing device 100 according to an embodiment of the present disclosure includes a band 101 and a plurality of microphones 102 arranged around the band 101. FIG. 1 illustrates a state in which the signal processing device 100 is attached around a wrist of a human.

In the embodiment, the microphones 102 are provided at four positions illustrated in FIG. 1 to facilitate detection of a movement of the wrist, as illustrated in FIG. 1. The number and the setting positions of the microphones 102 are not limited to the example illustrated in FIG. 1.

Each of the microphones 102 may be a directional microphone. The directivity may be in a vertical direction from a sound collection surface of each microphone, that is, directivity in a direction of an arrow of a broken line in FIG. 1. For example, when a user with the signal processing device 100 attached around the wrist moves the wrist vertically or laterally, wind noises occur with such a movement. Each of the microphones 102 has such a directivity, which enables the signal processing device 100 to detect a moving direction on the basis of a level of the wind noises.

The above has described an example of the external appearance of the signal processing device 100 according to the embodiment of the present disclosure using FIG. 1. The following will describe an example of a functional configuration of the signal processing device 100 according to the embodiment of the present disclosure.

1.2. Example of Functional Configuration

Figure 2:
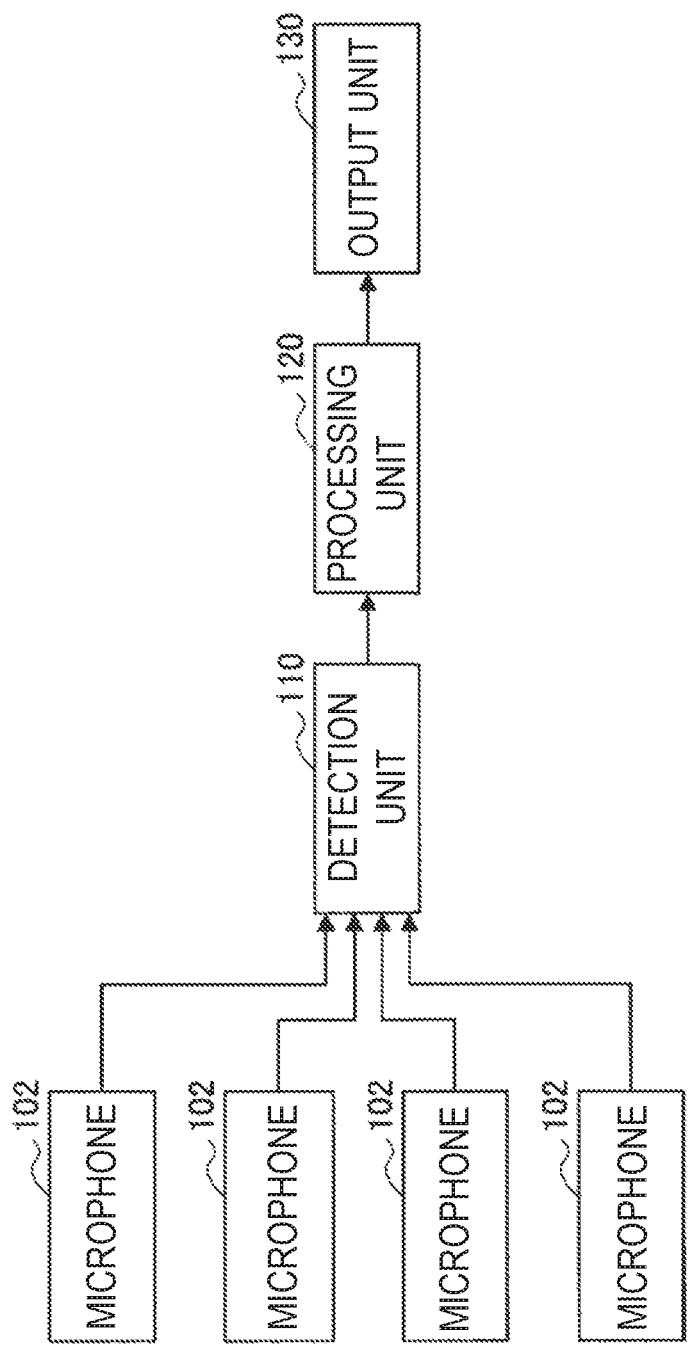
FIG. 2 is an explanatory diagram illustrating an example of a functional configuration of the signal processing device 100 according to the embodiment.

FIG. 2 is an explanatory diagram illustrating an example of a functional configuration of the signal processing device 100 according to the embodiment of the present disclosure. The following will describe an example of a functional configuration of the signal processing device 100 according to the embodiment of the present disclosure using FIG. 2.

As illustrated in FIG. 2, the signal processing device 100 according to the embodiment of the present disclosure includes the plurality of microphones 102, a detection unit 110, a processing unit 120, and an output unit 130.

As described above, the microphones 102 are provided to collect wind noises occurring in accordance with the movement of a region at which the signal processing device 100 is attached. Then, each of the microphones 102 may be a directional microphone, as described above. The microphones 102 output collected sound to the detection unit 110.

The detection unit 110 includes processors such as a central processing unit (CPU) and a digital signal processor (DSP), for example, and detects the details and levels of sound transmitted from each microphone 102. The detection unit 110 detects the details and levels of sound transmitted from the microphones 102 to detect a moving direction of the signal processing device 100. The detection unit 110 detects a moving direction of the signal processing device 100 on the basis of the details and levels of sound transmitted from the microphones 102, and then outputs the detection result to the processing unit 120. For example, the detection unit 110 detects which microphone 102 has collected wind noises of a level exceeding a given threshold.

The signal processing device 100 is configured to identify from which microphone 102 the sound transmitted to the detection unit 110 is transmitted. For example, the information identifying the microphone 102 may be added to the information of sound transmitted from each microphone 102, or an interface connecting the microphones 102 and the detection unit 110 may identify the microphone 102.

A method of detecting a moving direction of the signal processing device 100 by the detection unit 110 will be described. The detection unit 110 detects a moving direction of the signal processing device 100 on the basis of a difference of levels of wind noises collected by the microphones 102. With a movement in a certain direction, the microphone 102 provided in a vertical direction relative to such a direction obtains an aerodynamic sound (wind noises) of a high level.

Figure 3:
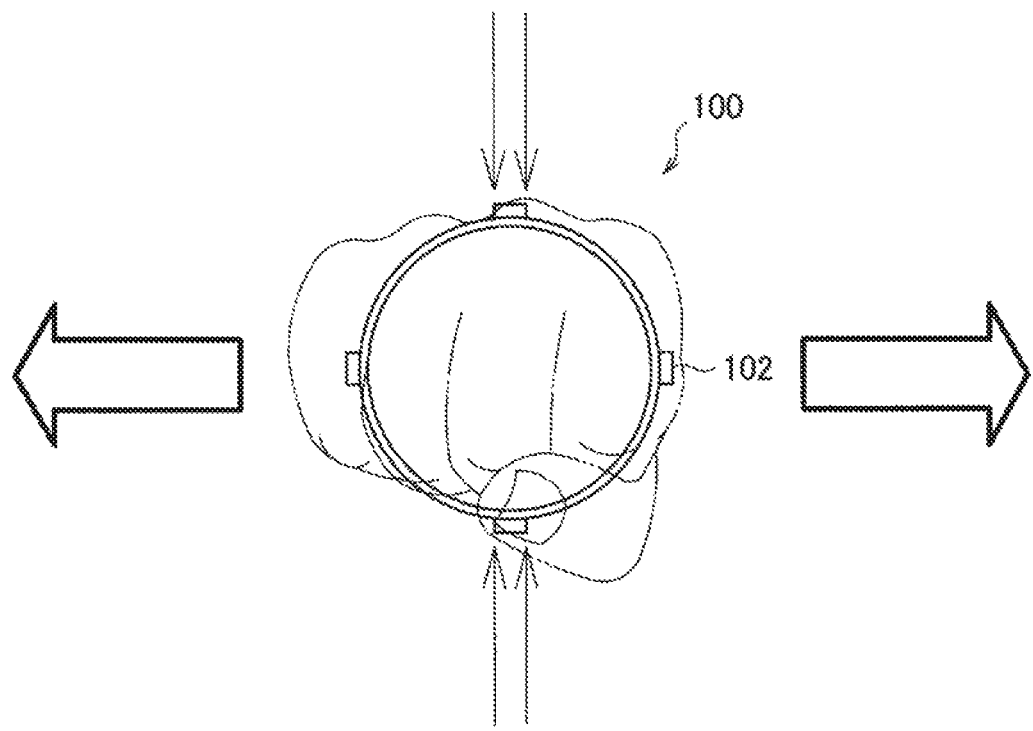
FIG. 3 is an explanatory diagram illustrating a situation of collection of wind noises by microphones 102 in a case where an arm is moved laterally.

FIG. 3 is an explanatory diagram illustrating a situation of collection of wind noises by the microphones 102 in a case where a user with the signal processing device 100 moves the arm laterally. Therefore, if the microphone 102 having collected sound of a high level exists, it is recognized that the arm is moved in the direction illustrated in FIG. 3.

Figure 4:
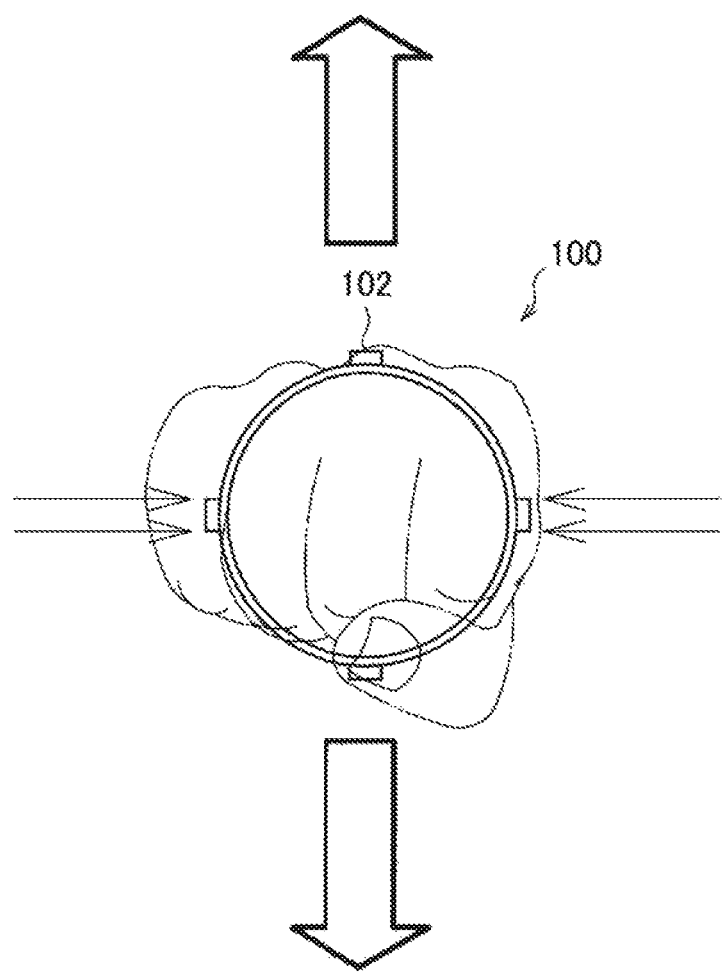
FIG. 4 is an explanatory diagram illustrating a situation of collection of wind noises by the microphones 102 in a case where an arm is moved vertically.

FIG. 4 is an explanatory diagram illustrating a situation of collection of wind noises by the microphones 102 in a case where a user with the signal processing device 100 moves the arm vertically. Therefore, if the microphone 102 having collected sound of a high level exists, it is recognized that the arm is moved in the direction illustrated in FIG. 4.

In this manner, if the microphone 102 having collected sound of a high level exists, the detection unit 110 detects which microphone 102 has collected wind noises of a level exceeding a given threshold to detect a moving direction of the signal processing device 100.

The microphone 102 can collect not only wind noises but also other various kinds of sound. However, the frequency of wind noises is considerably limited, and thus the detection unit 110 detects the presence or absence of sound at the frequency corresponding to the wind noises to determine whether or not the microphone 102 has collected wind noises. Between the microphone 102 and the detection unit 110, there may be provided a filter allowing only signals in a frequency band corresponding to wind noises to pass. Such a filter may be a bandpass filter or a high pass filter.

Note that to improve the detection accuracy of a moving direction, the signal processing device 100 may have a configuration in which a specific microphone 102 is provided at a specific position. For example, if the signal processing device 100 has a configuration in which a specific microphone 102 is positioned on the side of a back of a hand, the signal processing device 100 detects a moving direction more easily on the basis of the sound collection level of the specific microphone 102.

The processing unit 120 includes processors such as a CPU and a DSP, a storage medium such as a read only memory (ROM), a random access memory (RAM), and the like, and performs processing in accordance with a moving direction of the signal processing device 100 detected by the detection unit 110. The processing unit 120 performs, as processing in accordance with a moving direction of the signal processing device 100, generation of sound in accordance with a moving direction, effect processing on sound collected by the microphones 102, and the like.

For example, the processing unit 120 may generate different sound between the case of FIG. 3 in which a user with the signal processing device 100 attached around the wrist moves the wrist horizontally with the back of the hand upward and the case of FIG. 4 in which a user with the signal processing device 100 attached around the wrist moves the wrist vertically with the back of the hand upward. The sound generated by the processing unit 120 in such a manner can be output from the output unit 130 in the later stage.

Moreover, for example, the processing unit 120 may perform signal processing on a waveform of sound collected by the microphones 102. The effect processing performed by the processing unit 120 can include, for example, echo, reverberation, modulation by a low frequency, a speed change (time stretching), a pitch change (pitch shift), and the like. Note that the sound amplification processing may be regarded as a kind of effect processing. The processing unit 120 can perform, as effect processing, filter effects such as low pass, high pass, and bandpass, addition synthesis and subtraction synthesis with an oscillator (sine wave, sawtooth wave, triangular wave, rectangular wave, etc.). The processing unit 120 may perform, as signal processing, amplification processing on at least a part of frequency bands of sound collected by the microphones 102, effect processing, and the like, for example.

The processing unit 120 may regard an amplification amount, a frequency band to be amplified, and the contents of effect processing on sound collected by the microphones 102 as those specified by a user, or automatically determine them. In a case where the processing unit 120 automatically determine an amplification amount, a frequency band to be amplified, and the contents of effect processing on sound collected by the microphones 102, it may determine them in accordance with the detected details of the movement of the signal processing device 100, that is, the details of the movement of a region or a tool at which the signal processing device 100 is attached.

Moreover, the processing unit 120 can perform processing in accordance with the form of the output unit 130 described later. In a case where the output unit 130 is a vibrator, for example, the processing unit 120 can generate or determine a vibration pattern in accordance with a moving direction of the signal processing device 100. Moreover, in a case where the output unit 130 is a light emitting diode (LED), for example, the processing unit 120 can generate or determine a light emitting pattern in accordance with a moving direction of the signal processing device 100, and determine a light emission color.

The output unit 130 performs output based on signal processing performed by the processing unit 120. The output unit 130 may have various forms such as a speaker, a vibrator, an LED, a wireless communication interface, and the like, for example.

In a case where the output unit 130 is a speaker, for example, the output unit 130 may output sound generated by the processing unit 120 in accordance with a moving direction of the signal processing device 100. That is, the output unit 130 can output different sound depending on a moving direction of the signal processing device 100.

In a case where the output unit 130 is a vibrator, for example, the output unit 130 may vibrate in a vibration pattern generated by the processing unit 120 in accordance with a moving direction of the signal processing device 100. That is, the output unit 130 can output different sound depending on a moving direction of the signal processing device 100.

Moreover, in a case where the output unit 130 is an LED, for example, the output unit 130 may emit light in a light emitting pattern or color generated by the processing unit 120 in accordance with a moving direction of the signal processing device 100. That is, the output unit 130 can output different sound depending on a moving direction of the signal processing device 100.

Moreover, in a case where the output unit 130 is a wireless communication interface, for example, the output unit 130 may transmit sound generated by the processing unit 120 in accordance with a moving direction of the signal processing device 100 to another device. Such another device can be a speaker having a wireless communication function, a personal computer, a smartphone (high function portable telephone), a tablet-type portable terminal, a portable music reproducing device, a portable game machine, and the like, for example.

The signal processing device 100 according to the embodiment of the present disclosure has the configuration illustrated in FIG. 2, which makes it possible to detect a moving direction of a region at which the signal processing device 100 is attached without using a sensor.

1.3. Application Example

Figure 5:
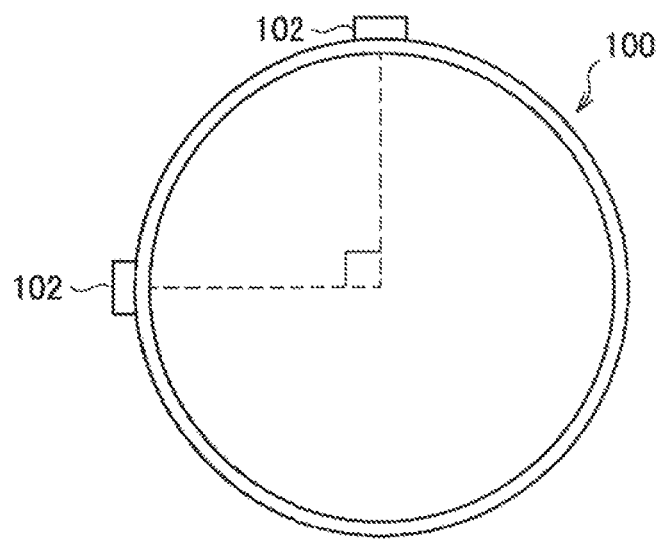
FIG. 5 is an explanatory diagram illustrating an application example of the signal processing device 100.

The signal processing device 100 may have various forms other than the form illustrated in FIG. 1. FIG. 1 illustrates the example of the external appearance of the signal processing device 100 with four microphones 102. However, the present disclosure is not limited to such an example. FIG. 5 is an explanatory diagram illustrating an application example of the signal processing device 100. As described above, to detect a movement in a horizontal direction and a vertical direction, it is sufficient if the microphones 102 are provided at two positions, as illustrated in FIG. 5, for example.

Figure 6:
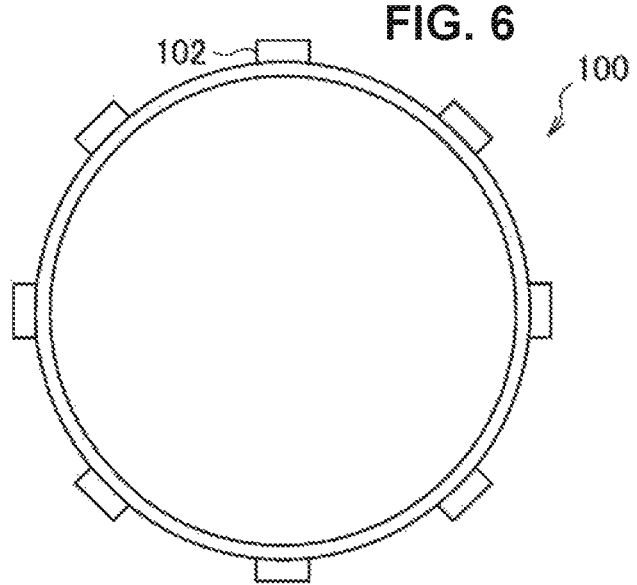
FIG. 6 is an explanatory diagram illustrating an application example of the signal processing device 100.

Moreover, with the increased number of microphones 102, the signal processing device 100 can detect with higher accuracy a moving direction of a region at which it is attached. FIG. 6 is an explanatory diagram illustrating an application example of the signal processing device 100. FIG. 6 illustrates the signal processing device 100 with eight microphones 102 arranged on the band 101 with substantially same intervals. With the eight microphones 102 provided in this manner, the signal processing device 100 can detect a movement not only in a horizontal direction and a vertical direction but also in an oblique direction.

With the increased number of microphones 102, the signal processing device 100 can detect with higher accuracy not only a moving direction of a region at which it is attached, but also a moving speed or a rotation angular speed of the region at which it is attached by monitoring a temporal change of the level of wind noises.

Figure 7:
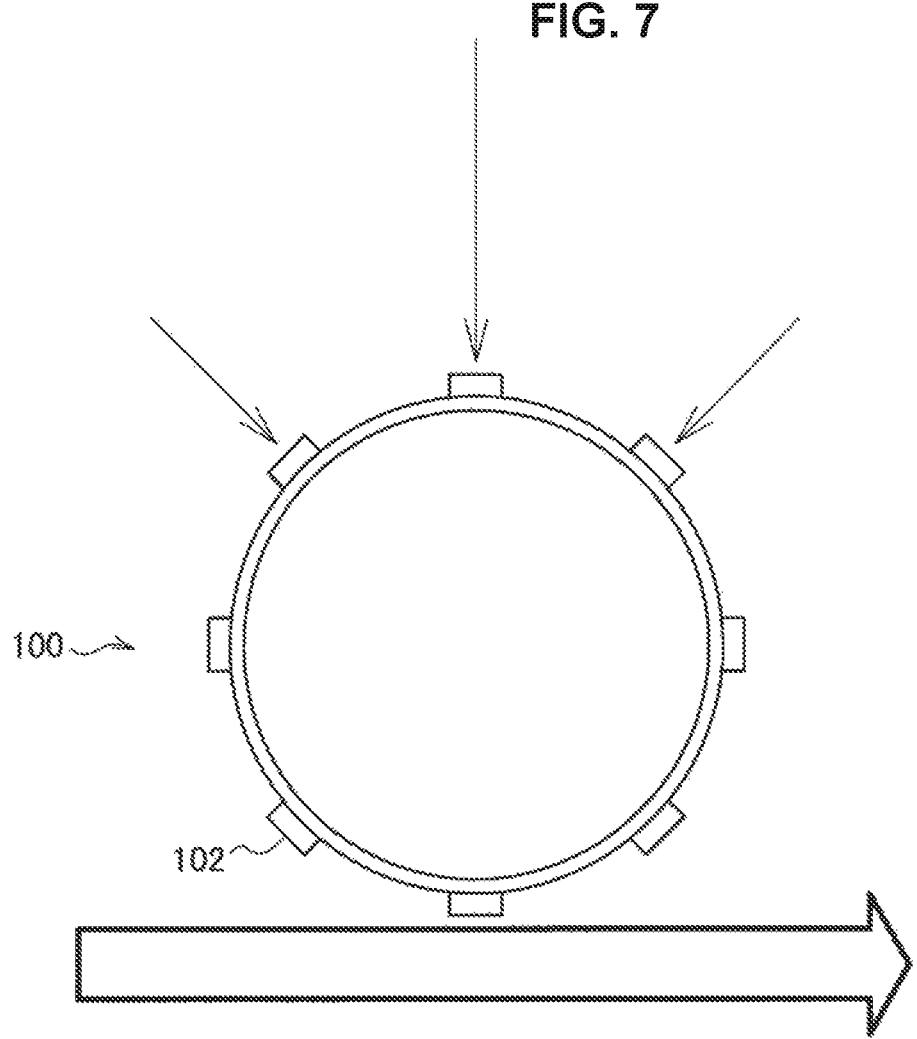
FIG. 7 is an explanatory diagram illustrating an application example of the signal processing device 100.

FIG. 7 is an explanatory diagram illustrating an application example of the signal processing device 100. FIG. 7 illustrates the signal processing device 100 with eight microphones 102 arranged on the band 101 with substantially same intervals. Moreover, FIG. 7 illustrates a situation in which an attachment region of the signal processing device 100 is moved from left to right in FIG. 7. If the moving speed is high, a level of wind noises is also high. Thus, the signal processing device 100 can estimate a moving speed of the attachment region of the signal processing device 100 on the basis of the temporal change of a level of wind noises collected by the microphones 102.

Figure 8:
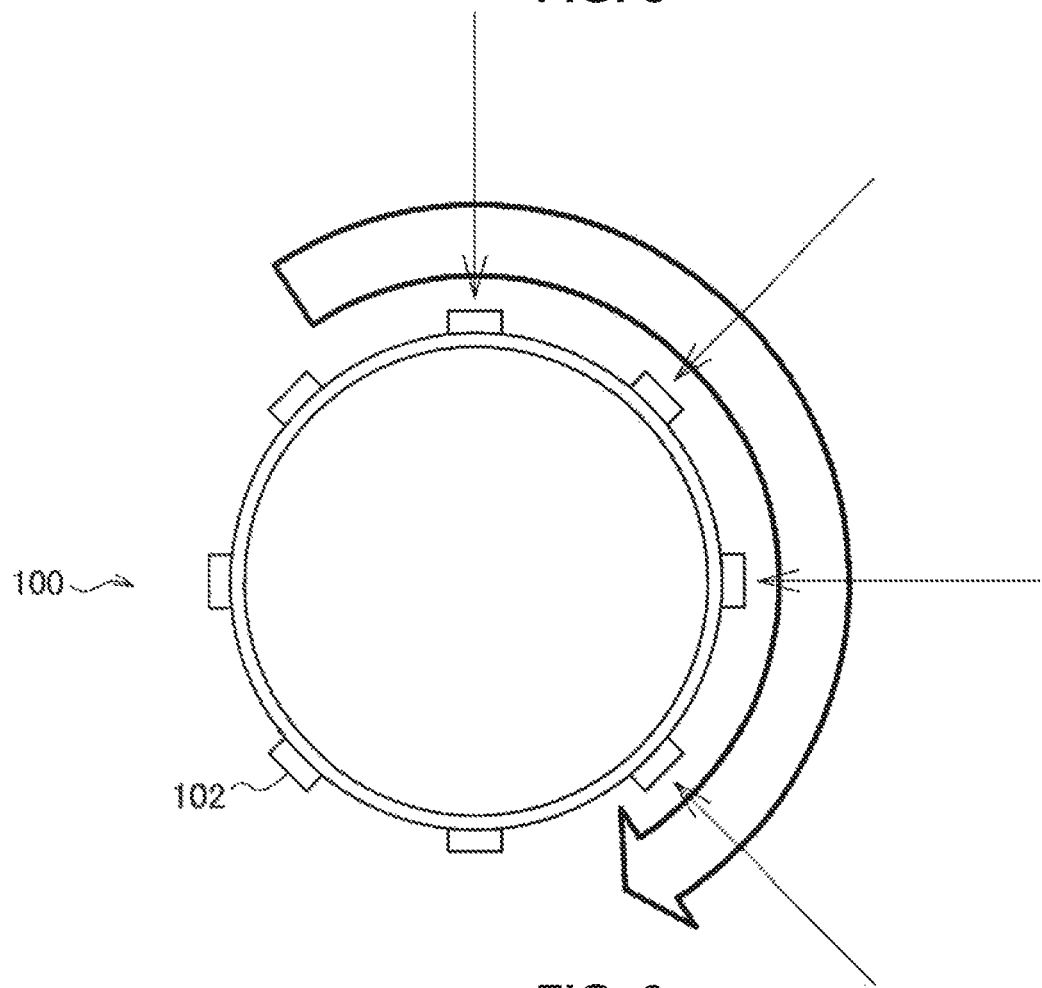
FIG. 8 is an explanatory diagram illustrating an application example of the signal processing device 100.

FIG. 8 is an explanatory diagram illustrating an application example of the signal processing device 100. FIG. 8 illustrates the signal processing device 100 with eight microphones 102 arranged on the band 101 with substantially same intervals. Moreover, FIG. 8 illustrates a situation in which the attachment region of the signal processing device 100 is rotated in a clockwise direction. If the rotation angular speed is high, the level of wind noises is also high. Thus, the signal processing device 100 can estimate a rotation angular speed of the attachment region of the signal processing device 100 on the basis of the temporal change of a level of wind noises collected by the microphones 102.

The signal processing device 100 may have various forms other than those described above. As described above, an object at which the signal processing device 100 is attached can be sporting goods, for example, such as a bat, a racket, and a golf club. Therefore, it is obvious that various forms may be assumed in accordance with a form of an object to which attachment is performed. The following will describe examples of the signal processing device 100 with reference to the enclosed drawings. However, it is obvious that the form of the signal processing device 100 is not limited to ones described in the following. FIG. 9 to FIG. 12 are explanatory diagrams illustrating application examples of the signal processing device 100.

Figure 9:
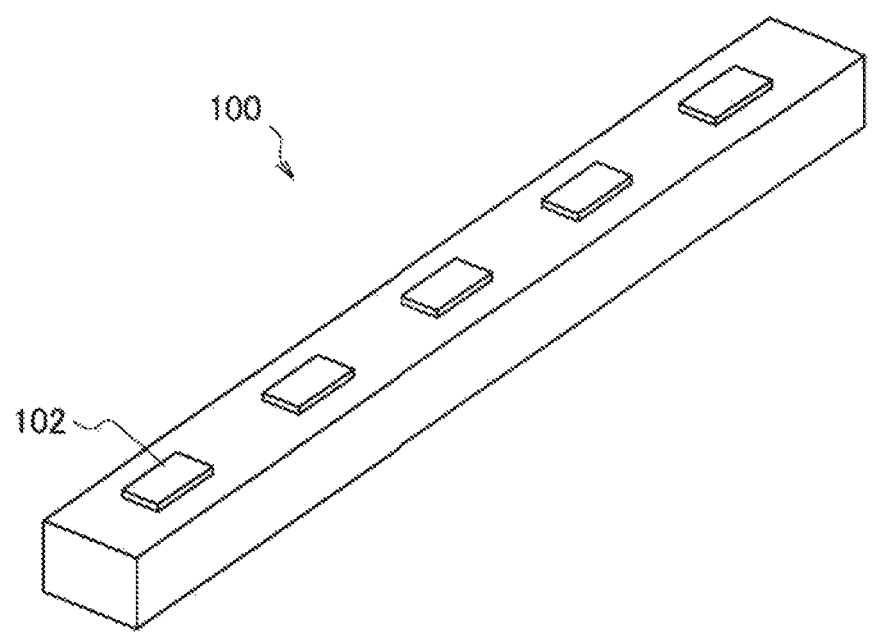
FIG. 9 is an explanatory diagram illustrating an application example of the signal processing device 100.
Figure 10:
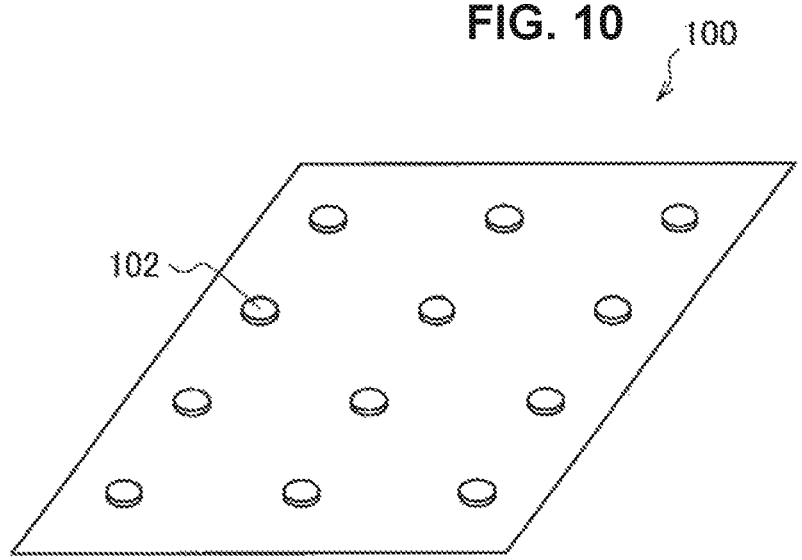
FIG. 10 is an explanatory diagram illustrating an application example of the signal processing device 100.

FIG. 9 is an explanatory diagram illustrating an example of the signal processing device 100 in which the plurality of microphones 102 is provided on a surface of a bar-shaped object. FIG. 10 is an explanatory diagram illustrating an example of the signal processing device 100 in which the plurality of microphones 102 is provided on a surface of a planar object. In this manner, the signal processing device 100 can estimate a moving direction and a moving speed of the signal processing device 100 itself, a moving direction and a moving speed of an attachment region of the signal processing device 100, and the like also by detecting the level of wind noises collected by the microphones 102 provided on a bar-shaped or planar object.

Figure 11:
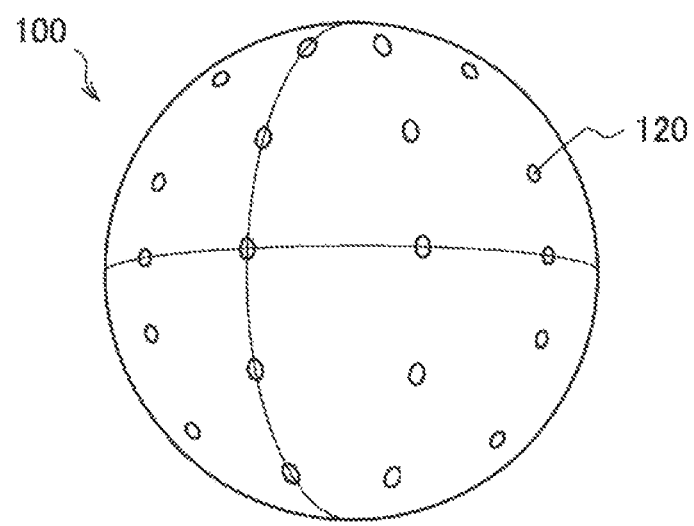
FIG. 11 is an explanatory diagram illustrating an application example of the signal processing device 100.
Figure 12:
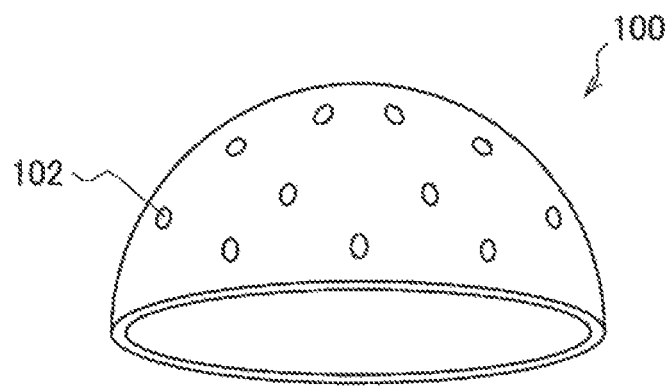
FIG. 12 is an explanatory diagram illustrating an application example of the signal processing device 100.

FIG. 11 is an explanatory diagram illustrating an example of the signal processing device 100 in which the plurality of microphones 102 is provided on a surface of a spherical object. Moreover, FIG. 12 is an explanatory diagram illustrating an example of the signal processing device 100 in which the plurality of microphones 102 is provided on a surface of a hemispherical object. In this manner, the signal processing device 100 can estimate a moving direction and a moving speed of the signal processing device 100 itself, a moving direction and a moving speed of an attachment region of the signal processing device 100, and the like also by detecting the level of wind noises collected by the microphones 102 provided on a spherical or hemispherical object.

For example, in a case where the signal processing device 100 has a shape of a helmet with the plurality of microphones 102 around it, it is attached on a head to estimate a moving direction, a moving speed, and the like of the head.

In each example, the positions at which the microphones are provided are preferably arranged with same intervals.

FIG. 1 and the like illustrate the examples of the signal processing device 100 in which the microphones 102 are provided at a plurality of positions. However, the present disclosure is not limited to such examples. The plurality of microphones 102 may be arranged collectively at one position.

Figure 13:
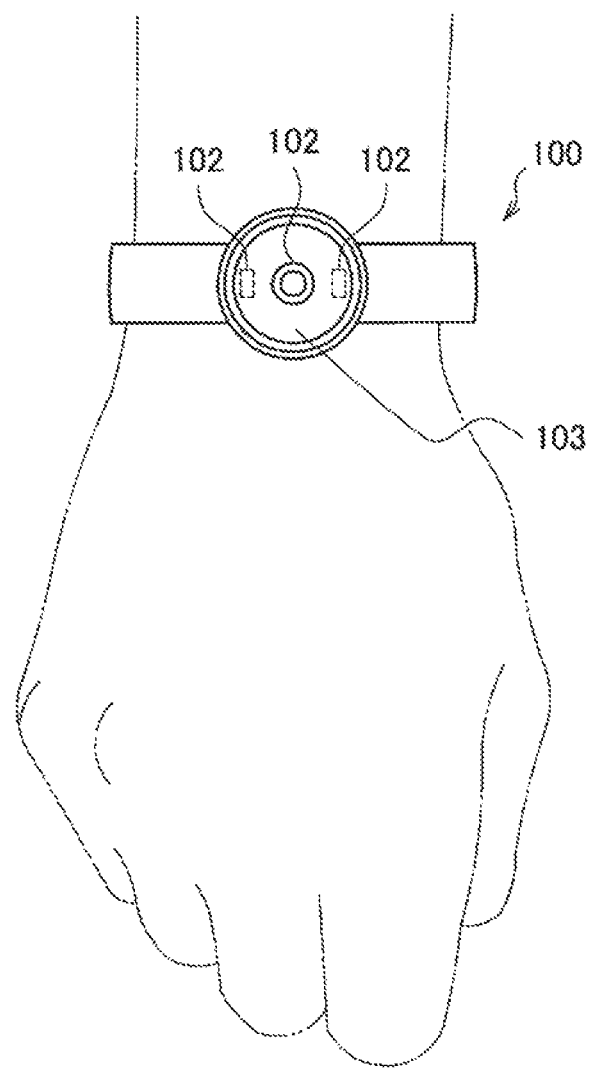
FIG. 13 is an explanatory diagram illustrating an application example of the signal processing device 100.
Figure 14:
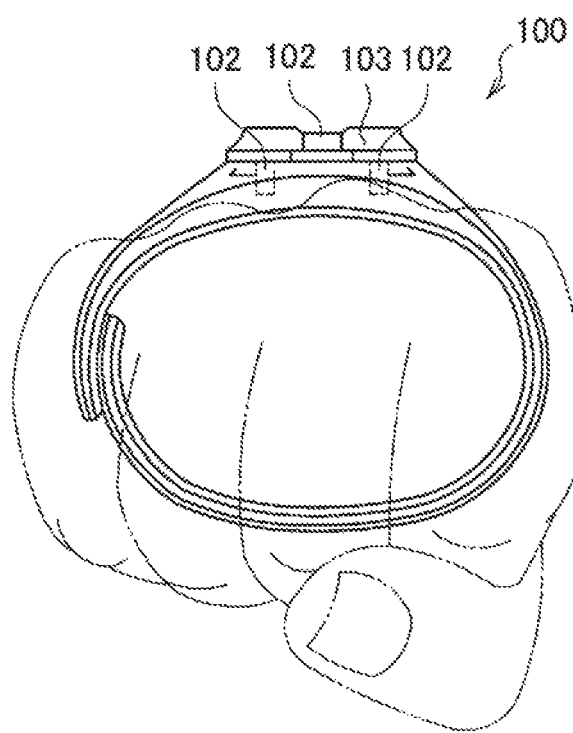
FIG. 14 is an explanatory diagram illustrating an application example of the signal processing device 100.
Figure 15:
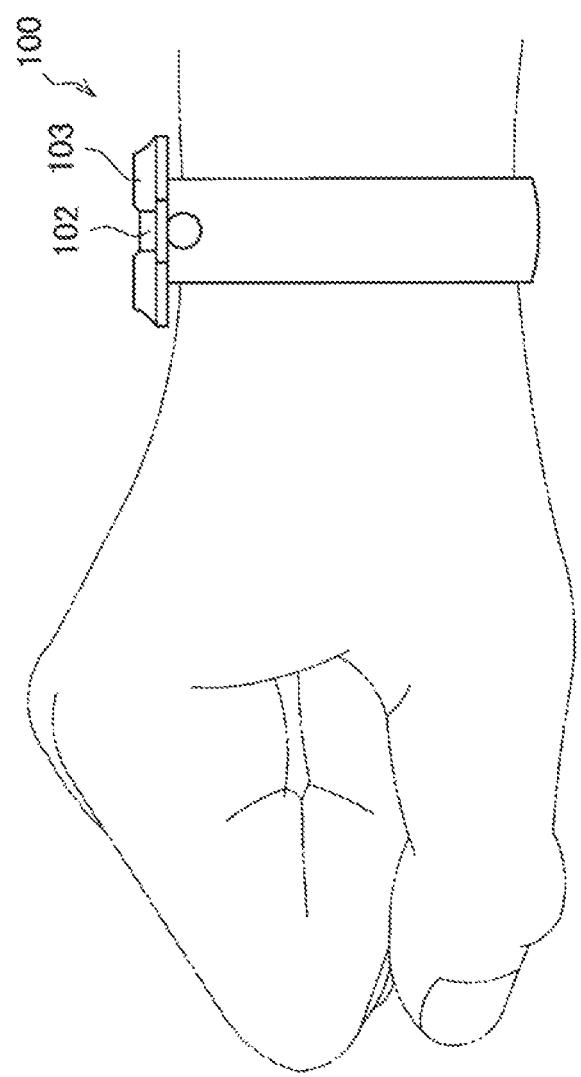
FIG. 15 is an explanatory diagram illustrating an application example of the signal processing device 100.

FIG. 13 to FIG. 15 are explanatory diagrams illustrating an example of the signal processing device 100 having a shape appropriate for attachment around a wrist. FIG. 13 is a plane view of the signal processing device 100. FIG. 14 is a side view of the signal processing device 100, viewed from one side surface thereof. FIG. 15 is a side view of the signal processing device 100, viewed from another side surface thereto.

The signal processing device 100 illustrated in FIG. 13 to FIG. 15 is configured so that the plurality of microphones 102 is positioned on the side of a back of a hand when it is attached around a wrist. The plurality of microphones 102 is covered by a cover 103. The cover 103 has a shape facilitating collection of wind noises on the upper side and in a lateral direction of the signal processing device 100. In the signal processing device 100 illustrated in FIG. 13 to FIG. 15, the plurality of microphones 102 is positioned to collect wind noises on the upper side and in a lateral direction.

Note that the cover 103 covering the plurality of microphones 102 may include the output unit 130 in the configuration example of the signal processing device 100 described using FIG. 2. For example, the cover 103 may include an LED changing its light emitting pattern or light emission color in accordance with a moving direction of a wrist. Moreover, for example, the cover 103 may include a vibrator changing its vibration pattern or vibration time in accordance with a moving direction of a wrist.

Also with such forms, the signal processing device 100 can estimate a moving direction and a moving speed of an attachment region.

Furthermore, the signal processing device 100 includes the plurality of microphones 102, which makes it possible to estimate not only a moving direction, a moving speed, and the like of an attachment region but also a moving direction, a moving speed, and the like of an adjacent object.

Figure 16:
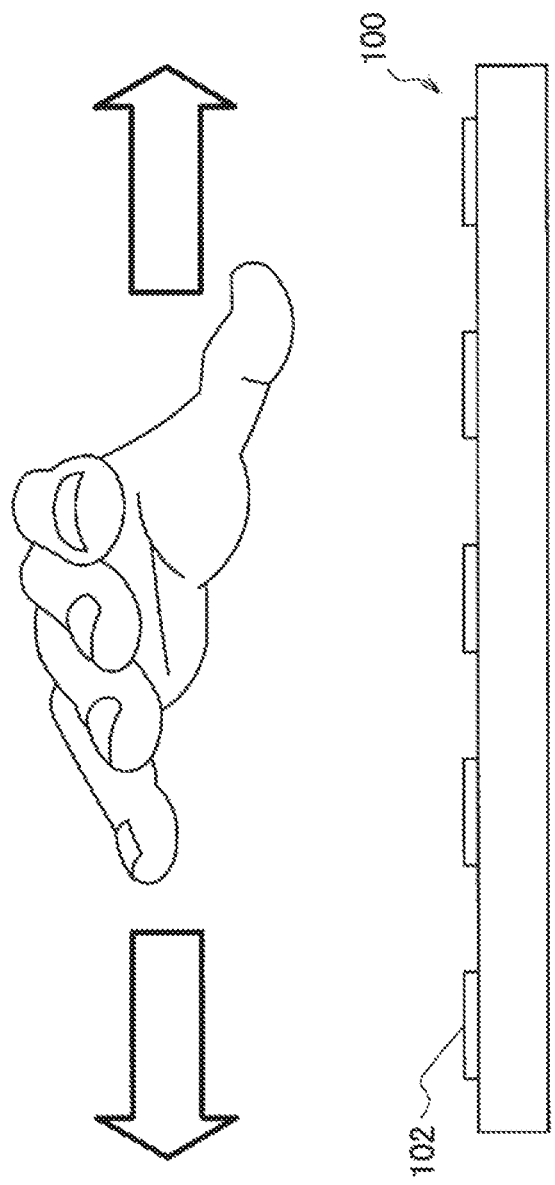
FIG. 16 is an explanatory diagram illustrating an application example of the signal processing device 100.

FIG. 16 is an explanatory diagram illustrating an example of the signal processing device 100. With the plurality of microphones 102 provided on a surface of a bar-shaped object, as illustrated in FIG. 9, for example, when a human moves the hand or the like above the microphones, aerodynamic sound occurs with the movement. The signal processing device 100 collects such aerodynamic sound using the microphones 102 and analyzes the change of the aerodynamic sound to estimate a direction in which an object such as a hand has moved, a speed at which the object has moved, and the like above the surface of the signal processing device 100.

Moreover, the detection unit 110 may also synthesize wind noises collected by the plurality of microphones 102 to detect the movement of the signal processing device 100. This does not obtain wind noises with a movement in a specific direction but wind noises with a movement in various directions. Note that the synthesis of wind noises collected by the plurality of microphones 102 may be performed by adding wind noises collected by each of the microphones 102, or adding wind noises at a certain level or higher.

Figure 17:
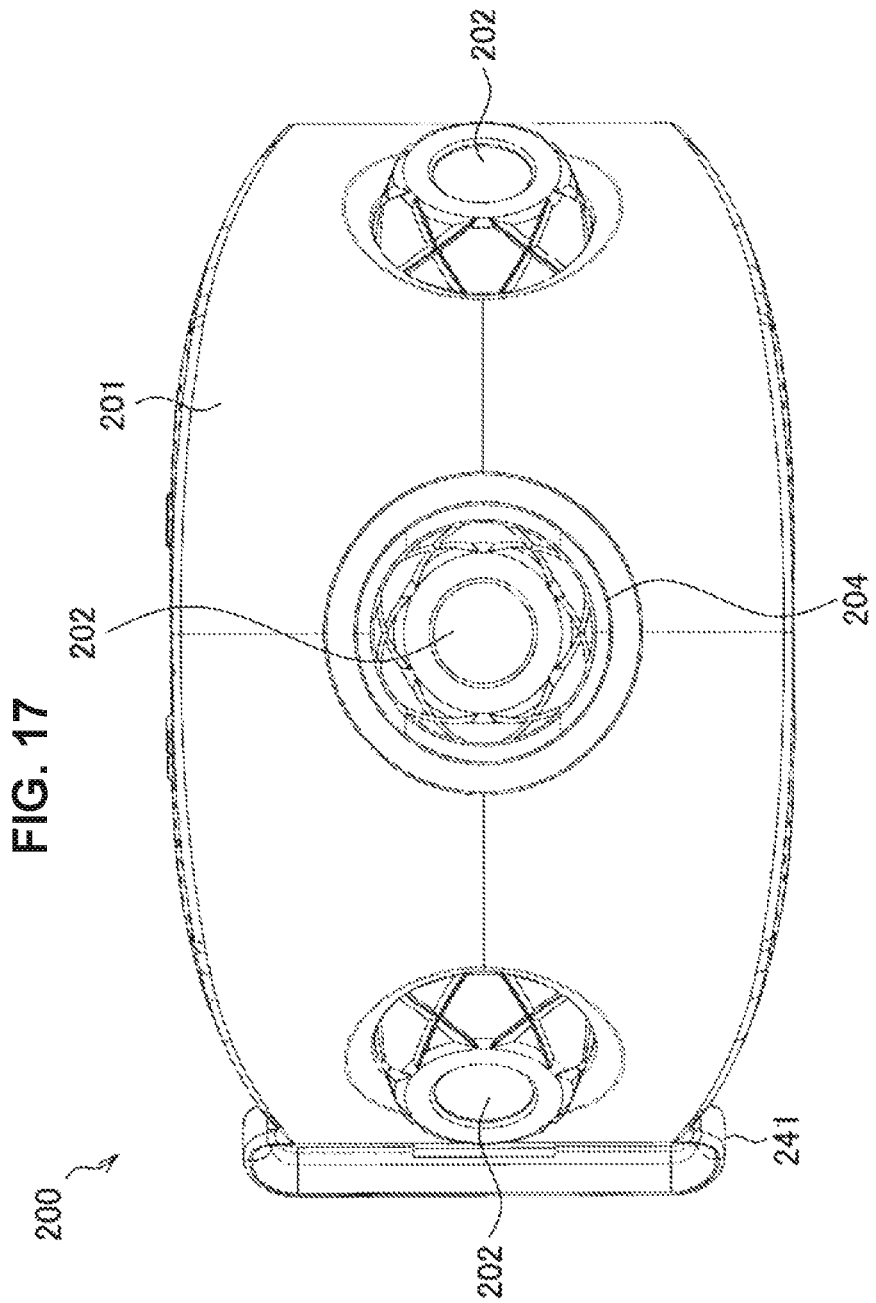
FIG. 17 is an explanatory diagram illustrating an example of an external appearance of a signal processing device 200.
Figure 18:
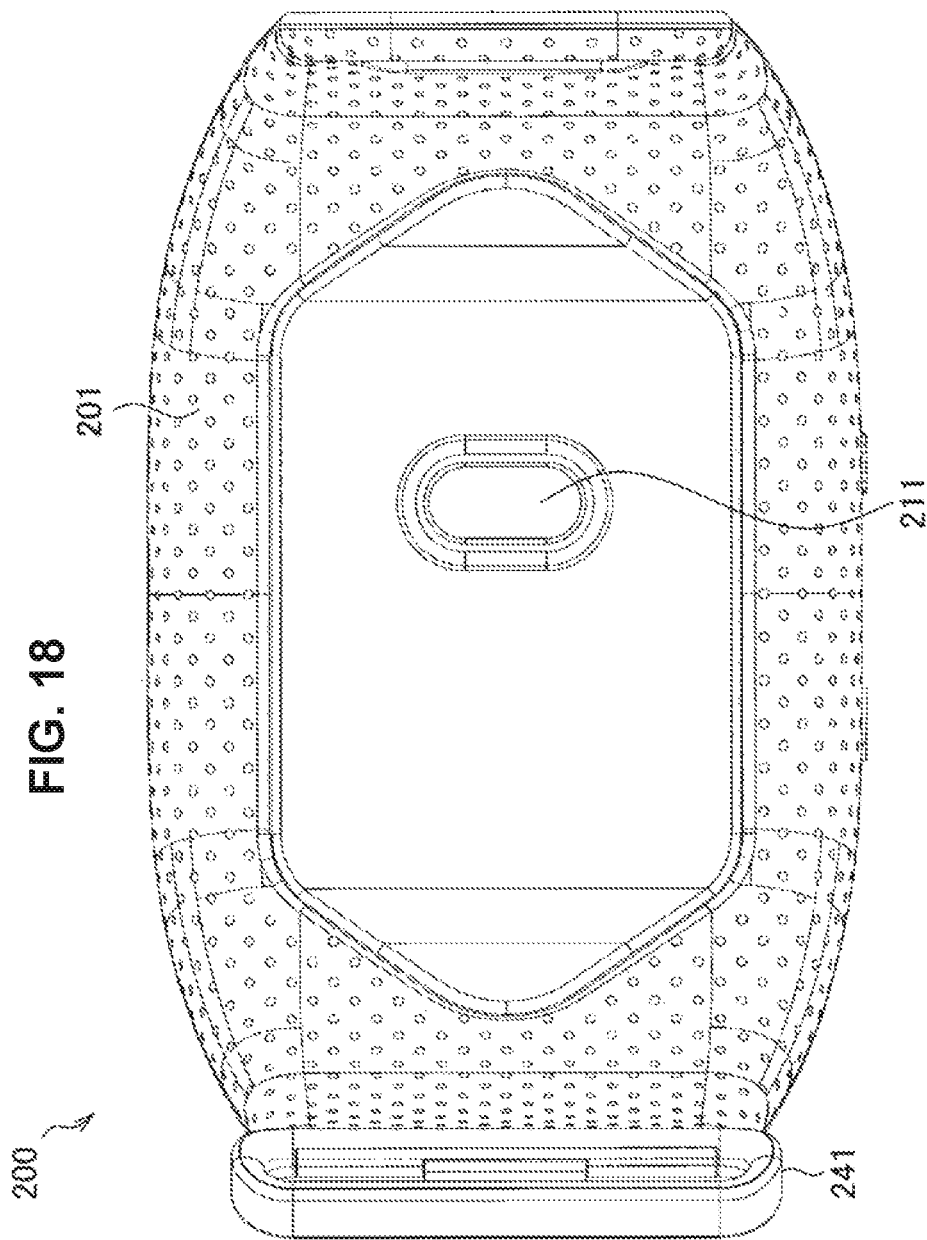
FIG. 18 is an explanatory diagram illustrating an example of an external appearance of the signal processing device 200.
Figure 19:
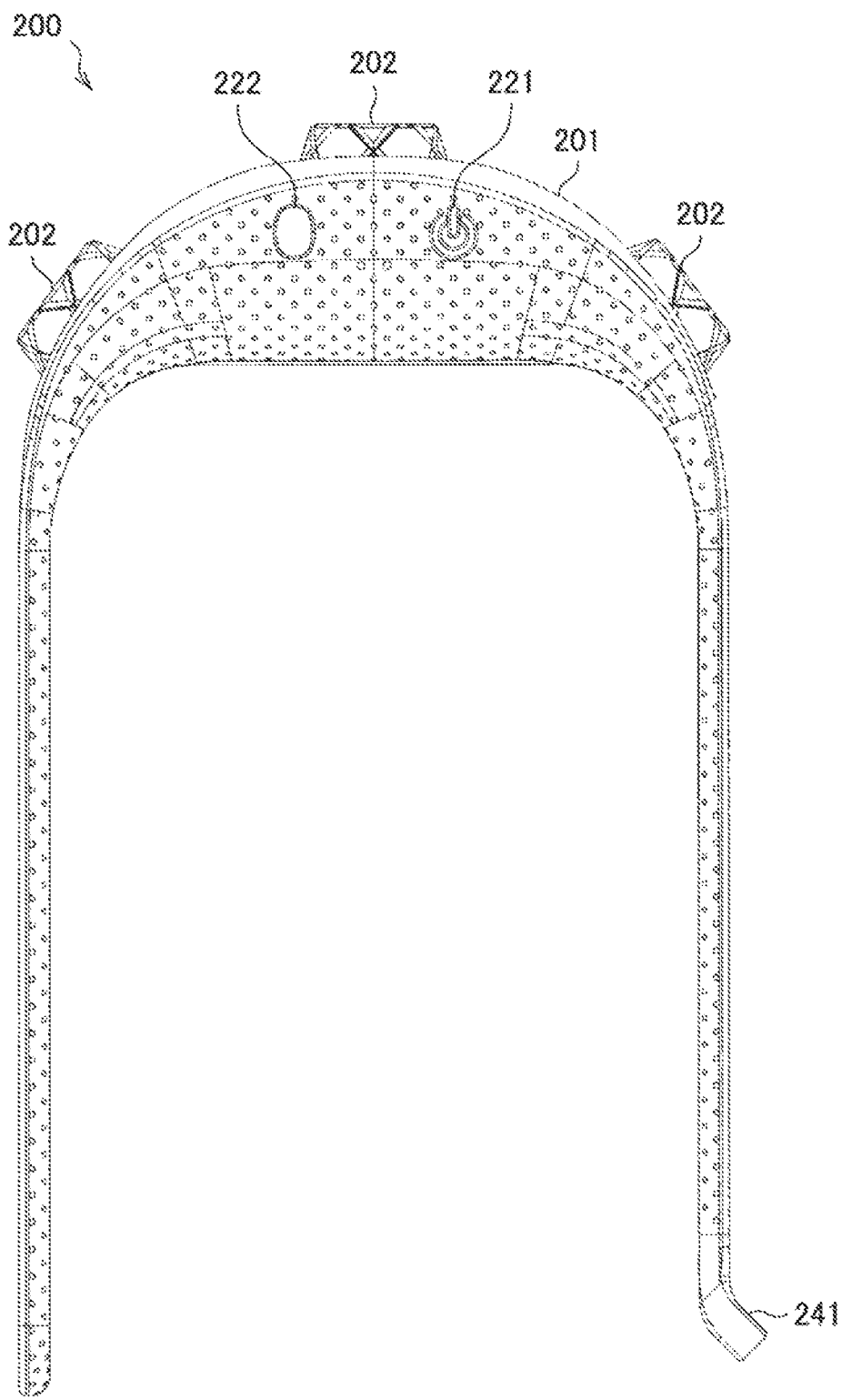
FIG. 19 is an explanatory diagram illustrating an example of an external appearance of the signal processing device 200.
Figure 20:
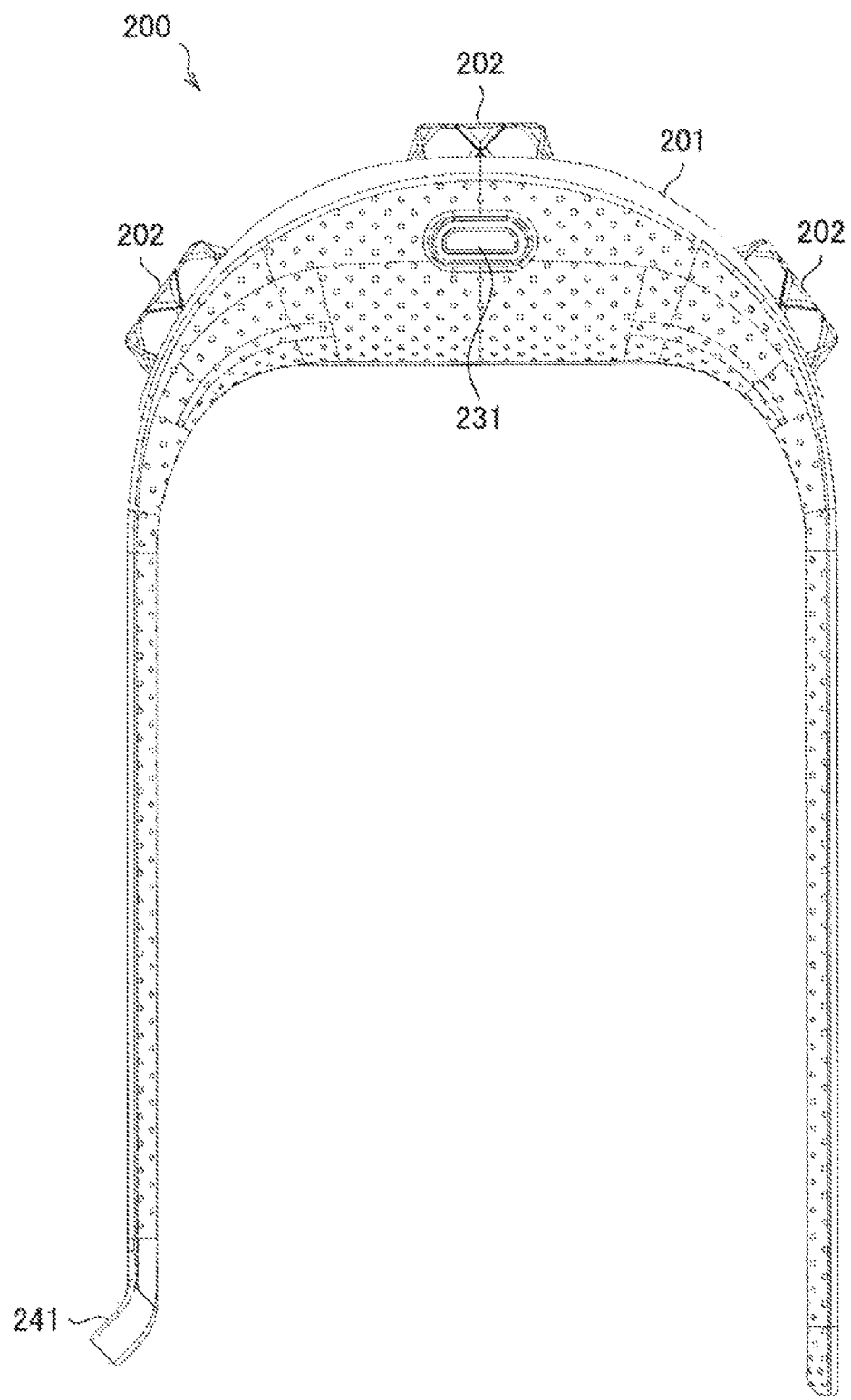
FIG. 20 is an explanatory diagram illustrating an example of an external appearance of the signal processing device 200.
Figure 21:
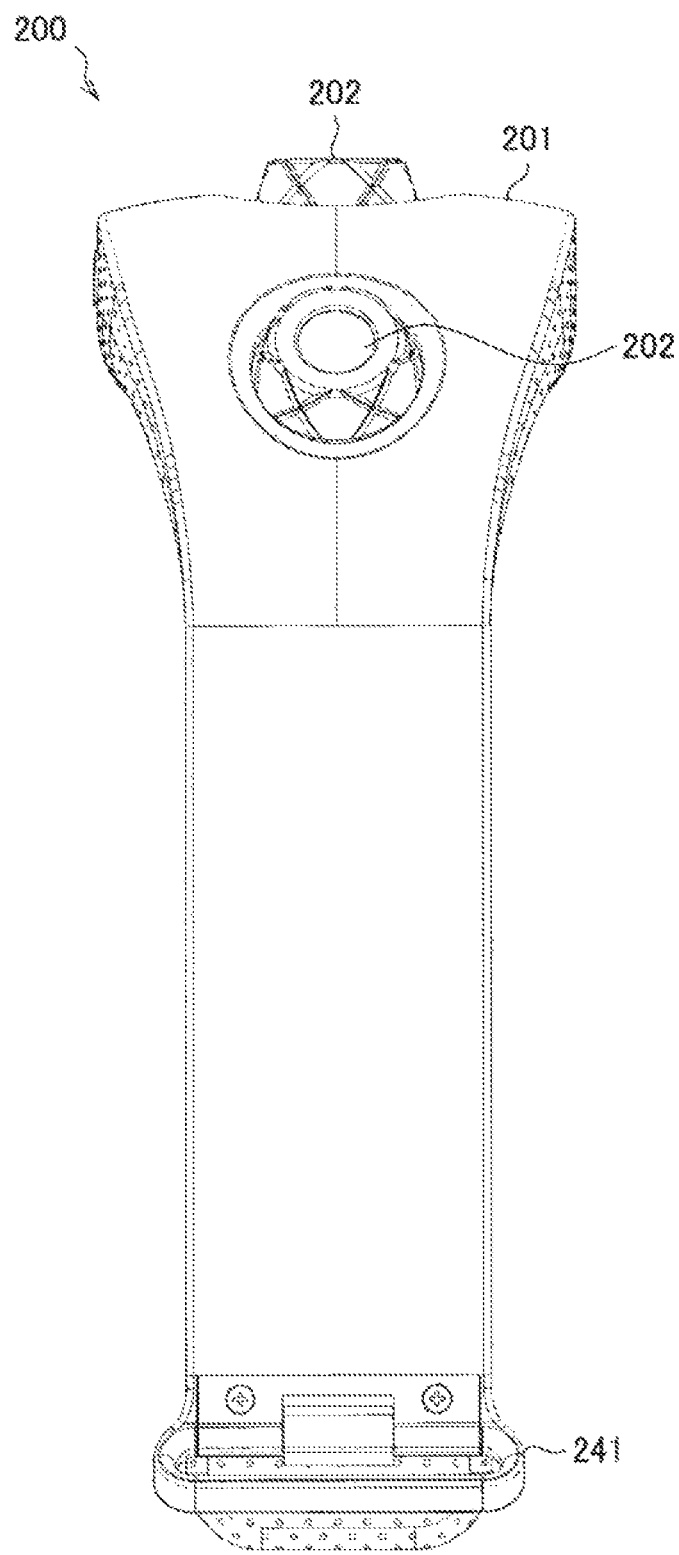
FIG. 21 is an explanatory diagram illustrating an example of an external appearance of the signal processing device 200.
Figure 22:
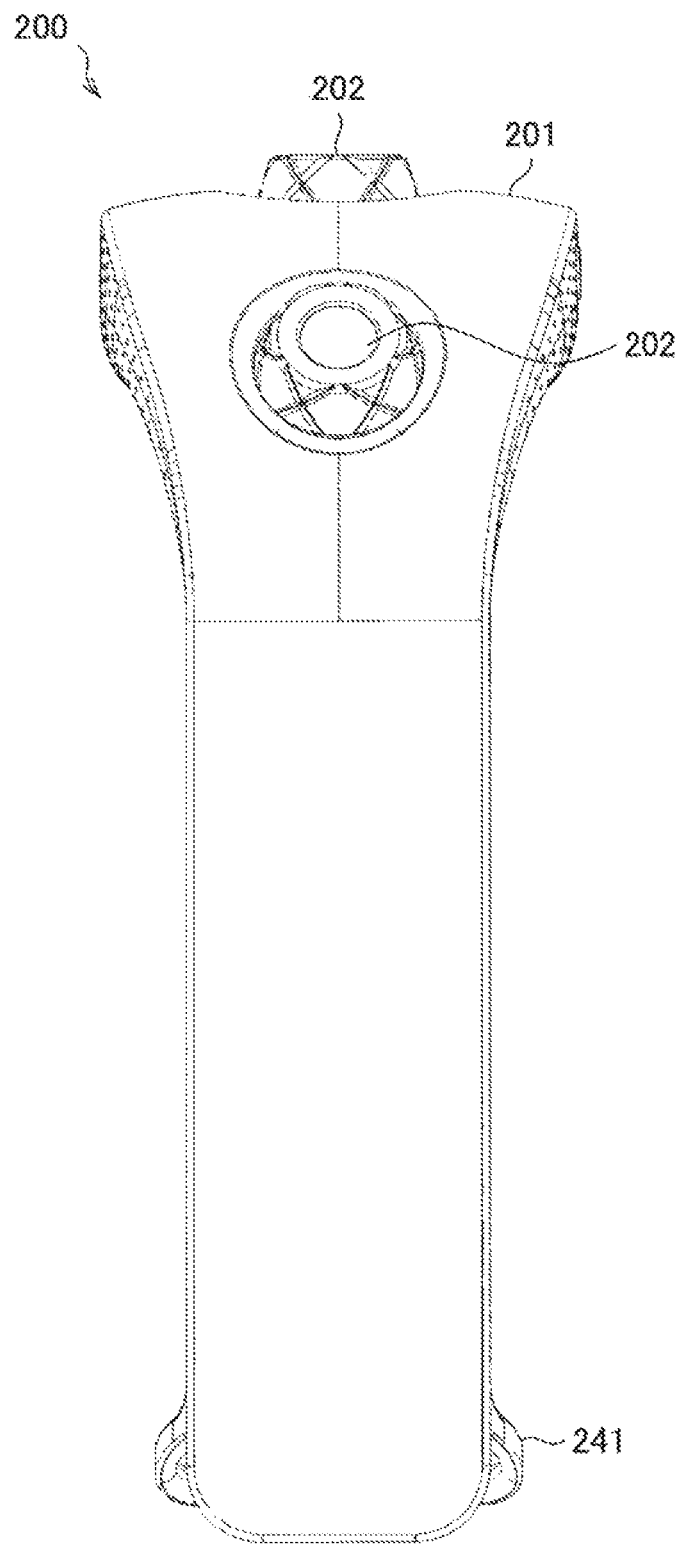
FIG. 22 is an explanatory diagram illustrating an example of an external appearance of the signal processing device 200.

FIGS. 17 to 22 are explanatory diagrams illustrating an example of an external appearance of a signal processing device 200 according to another embodiment of the present disclosure. FIG. 17 is an explanatory diagram illustrating a planar view of the signal processing device 200. FIG. 18 is an explanatory diagram illustrating a bottom view of the signal processing device 200. FIG. 19 and FIG. 20 are explanatory diagrams illustrating a front view of the signal processing device 200. FIG. 21 and FIG. 22 are explanatory diagrams illustrating a side view of the signal processing device 200.

Similarly to the signal processing device 100 described above, the signal processing device 200 illustrated in FIG. 17 to FIG. 22 analyzes the details of wind noises (aerodynamic sound) collected by a plurality of microphones to analyze a moving direction, a moving speed, and the like of a region at which it is attached. The signal processing device 200 can have a configuration similar to the functional configuration example of the signal processing device 100 illustrated in FIG. 2, for example. Therefore, when a user with the signal processing device 200 attached around the wrist move the wrist, for example, the signal processing device 200 detects differences of levels of wind noises collected by each of microphone parts 202 to determine in which direction the user moves the wrist.

In the signal processing device 200 illustrated in FIG. 17 to FIG. 22, the plurality of microphone parts 202 is provided on a surface of a band part 201 for fixing the signal processing device 200 on a wrist of a user. Moreover, in the signal processing device 200, a light emitting part 204 using LEDs and the like is provided around the microphone part 202. Moreover, the signal processing device 200 includes a pairing button 211 for performing pairing as preparation for communication with another terminal and the like, a power button 221 for allowing a user to turn on and off the power of the signal processing device 200, and an operation button 222 for performing operation of the signal processing device 200. Moreover, the signal processing device 200 includes a charging terminal 231 for charging a buttery that is provided inside and not illustrated. Moreover, the signal processing device 200 includes, at one end of the band part 201, a fastening tool 241 for fixing the band part 201 around an arm.

Note that the signal processing device 200 may include a speaker although it is not illustrated in FIG. 17 to FIG. 22. With a speaker, the signal processing device 200 performs signal processing based on signal waveforms of wind noises collected by the microphone parts 202 and can output sound based on the signal processing from the speaker.

The plurality of (three in the examples illustrated in FIG. 17 to FIG. 22) microphone parts 202 is provided on the band part 201. The microphone parts 202 are preferably provided at positions symmetrical to each other in a plane view or side view. With the signal processing device 200 attached around a wrist of a human, for example, when the human moves the arm with the signal processing device 200, the microphone parts 202 collect wind noises. Provided at different positions of the band part 201, the microphones 202 can collect wind noises in various directions. Moreover, the signal processing device 200 includes the microphone parts 202 at the positions illustrated in FIG. 17 to FIG. 22, and thus can collect sufficient wind noises for performing signal processing.

Moreover, the microphone part 202 may have a shape projecting from the band part 201, as illustrated in FIG. 17 and the like. With the shape projecting from the band part 201, the microphone part 202 can collect a larger amount of wind noises. Moreover, the knurled cutting work may be applied to the microphone parts 202, as illustrated in FIG. 17 and the like. In a case where the knurled cutting work is applied, the microphone part 202 can collect a larger amount of wind noises.

With such a configuration, the signal processing device 200 analyzes the details of wind noises collected by the microphones to detect, without using a motion sensor sensing movements, the movement of the signal processing device 200 and analyze a moving direction, a moving speed, and the like of a region at which the signal processing device 200 is attached.

2. Summary

As described above, the embodiment of the present disclosure provides the signal processing device 100, 200 capable of analyzing a moving direction, a moving speed, and the like of a region at which it is attached by analyzing the details of wind noises (aerodynamic sound) collected by the plurality of microphones.

The signal processing device 100, 200 according to the embodiment of the present disclosure analyzes the details of wind noises collected by the microphones to estimate, without using a motion sensor sensing movements, information of the movement related to the signal processing device 100, 200 such as a movement of the signal processing device 100, 200 itself, a movement of a region at which the signal processing device 100, 200 is attached, and a movement of an object adjacent to the signal processing device 100, 200, for example.

It is also possible to create a computer program for causing hardware such as a CPU, ROM, and RAM, which are embedded in each device, to execute functions equivalent to the configuration of each device. Moreover, it is also possible to provide a storage medium having the computer program stored therein. In addition, respective functional blocks illustrated in the functional block diagrams may be implemented by hardware or hardware circuits, such that a series of processes may be implemented by the hardware or the hardware circuits.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A signal processing device, including: a plurality of sound collection units that is arranged at given positions; and a detection unit configured to detect, from respective sounds that have occurred in accordance with a movement of a region to which attachment is performed and have been collected by the sound collection units, a direction of the movement of the region.

(2)

The signal processing device according to (1), in which the detection unit detects the direction of the movement on the basis of a position of the sound collection unit having collected a sound at a level exceeding a given threshold.

(3)

The signal processing device according to (1) or (2), in which the detection unit detects the direction of the movement on the basis of temporal changes of levels of sounds collected by the respective sound collection units.

(4)

The signal processing device according to any of (1) to (3), further including: a processing unit configured to perform, on the basis of sounds collected by the sound collection units, effect processing on the sounds.

(5)

The signal processing device according to any of (1) to (4), in which the sound collection unit is a microphone having directivity.

(6)

The signal processing device according to (5), in which the microphone has directivity in a vertical direction relative to a sound collection surface.

(7)

The signal processing device according to any of (1) to (6), in which the detection unit estimates a speed of the movement from sounds collected by the sound collection units.

(8)

The signal processing device according to any of (1) to (7), in which the detection unit estimates a rotation angular speed of the movement from sounds collected by the sound collection units.

(9)

The signal processing device according to any of (1) to (8), in which the signal processing device is attached at a region to be moved.

(10)

The signal processing device according to any of (1) to (9), in which the sound collection units are arranged on a circular band.

(11)

The signal processing device according to any of (1) to (9), in which the sound collection units are arranged on a bar-shaped object.

(12)

The signal processing device according to any of (1) to (9), in which the sound collection units are arranged on a planar object.

(13)

The signal processing device according to any of (1) to (9), in which the sound collection units are arranged on a spherical object.

(14)

The signal processing device according to any of (1) to (9), in which the sound collection units are arranged on a hemispherical object.

(15)

A signal processing method, including: detecting, on the basis of respective sounds that have been collected by a plurality of sound collection units arranged at given positions and have occurred in accordance with a movement of a region to which the sound collection units are attached, a direction of the movement of the region.

REFERENCE SIGNS LIST

100 signal processing device
102 microphone

The invention claimed is:

1. A signal processing device, comprising:
   a plurality of sound collection units configured to collect a plurality of sounds generated by movement of a region, wherein
      the plurality of sound collection units is arranged at a plurality of positions, and
      the signal processing device is attached to the region; and
   a detection unit configured to:
      detect a sound collection unit from the plurality of sound collection units, based on a level of sound collected by the sound collection unit,
         wherein the level of the sound collected by the detected sound collection unit exceeds a threshold value; and
      detect a direction of the movement of the region, based on the detection of the sound collection unit.

2. The signal processing device according to claim 1, wherein the direction of the movement of the region is detected based on a position of the detected sound collection unit.

3. The signal processing device according to claim 1, wherein the direction of the movement of the region is detected based on temporal changes of levels of the plurality of sounds collected by the plurality of sound collection units.

4. The signal processing device according to claim 1, further comprising a processing unit configured to perform effect processing on the plurality of sounds collected by the plurality of sound collection units.

5. The signal processing device according to claim 1, wherein the plurality of sound collection units comprises a microphone having directivity.

6. The signal processing device according to claim 5, wherein the microphone has the directivity in a vertical direction relative to a sound collection surface of the microphone.

7. The signal processing device according to claim 1, wherein the detection unit is further configured to estimate a speed of the movement of the region from the plurality of sounds collected by the plurality of sound collection units.

8. The signal processing device according to claim 1, wherein the detection unit is further configured to estimate a rotation angular speed of the movement of the region, from the plurality of sounds collected by the plurality of sound collection units.

9. The signal processing device according to claim 1, wherein the plurality of sound collection units is arranged on a circular band.

10. The signal processing device according to claim 1, wherein the plurality of sound collection units is arranged on a bar-shaped object.

11. The signal processing device according to claim 1, wherein the plurality of sound collection units is arranged on a planar object.

12. The signal processing device according to claim 1, wherein the plurality of sound collection units is arranged on a spherical object.

13. The signal processing device according to claim 1, wherein the plurality of sound collection units is arranged on a hemispherical object.

14. A signal processing method, comprising:

collecting, by a plurality of sound collection units, a plurality of sounds generated by movement of a region, wherein the plurality of sound collection units is arranged at a plurality of positions, and the plurality of sound collection units is attached to the region;

detecting a sound collection unit from the plurality of sound collection units, based on a level of sound collected by the sound collection unit, wherein the level of sound collected by the detected sound collection unit exceeds a threshold; and detecting a direction of the movement of the region, based on the detection of the sound collection unit.

\* \* \* \* \*